US012214028B2

(12) United States Patent
Vidal Alvarez et al.

(10) Patent No.: US 12,214,028 B2
(45) Date of Patent: Feb. 4, 2025

(54) **IMMUNOGENIC FORMULATION THAT INDUCES PROTECTION AGAINST SHIGA TOXIN-PRODUCING *ESCHERICHIA COLI* (STEC)**

(71) Applicant: UNIVERSIDAD DE CHILE, Santiago (CL)

(72) Inventors: Roberto Mauricio Vidal Alvarez, Santiago (CL); Felipe Antonio Del Canto Fuentes, Santiago (CL); David Arturo Montero Forero, Santiago (CL); Juan Carlos Salazar Garrido, Santiago (CL)

(73) Assignee: UNIVERSIDAD DE CHILE, Santiago (CL)

( * ) Notice: Subject to any disclaimer, the term of this patent is extended or adjusted under 35 U.S.C. 154(b) by 382 days.

(21) Appl. No.: 17/615,554

(22) PCT Filed: May 31, 2019

(86) PCT No.: PCT/IB2019/054554
§ 371 (c)(1),
(2) Date: Nov. 30, 2021

(87) PCT Pub. No.: WO2020/240268
PCT Pub. Date: Dec. 3, 2020

(65) Prior Publication Data
US 2022/0233672 A1    Jul. 28, 2022

(51) Int. Cl.
*A61K 39/02*    (2006.01)
*A61K 39/108*   (2006.01)
*A61K 47/64*    (2017.01)
*A61K 47/69*    (2017.01)
*A61P 31/04*    (2006.01)
*C07K 14/245*   (2006.01)
*A61K 39/00*    (2006.01)

(52) U.S. Cl.
CPC ...... *A61K 39/0258* (2013.01); *A61K 47/6415* (2017.08); *A61K 47/6917* (2017.08); *A61P 31/04* (2018.01); *C07K 14/245* (2013.01); *A61K 2039/575* (2013.01)

(58) Field of Classification Search
None
See application file for complete search history.

(56) References Cited

U.S. PATENT DOCUMENTS

2012/0207776 A1    8/2012    Serino et al.

FOREIGN PATENT DOCUMENTS

| CN | 105821065 | 8/2016 |
| WO | 2015/164989 | 11/2015 |

OTHER PUBLICATIONS

Devos et al., (Proteins: Structure, Function and Genetics, 2000, vol. 41: 98-107).*
Whisstock et al., (Quarterly Reviews of Biophysics 2003, vol. 36 (3): 307-340).*
Witowski et al., (Biochemistry 38:11643-11650, 1999).*
Kisselev L., (Structure, 2002, vol. 10: 8-9).*
Mikayama et al. (Nov. 1993. Proc.Natl.Acad.Sci. USA, vol. 90: 10056-10060).*
Rudinger et al. (Jun. 1976. Peptide Hormones. Biol. Council. pp. 5-7).*
Altschul, S. F. et al., "Basic Local Alignment Search Tool," National Center for Biotechnology Information National Library of Medicine, National Institutes of Health Bethesda, MD, J. Mol. Biol., vol. 215, 1990, pp. 403-410.
Altschul, S. F. et al., "Gapped BLAST and PSI-BLAST: a new generation of protein database search programs," National Center for Biotechnology Information National Library of Medicine, National Institutes of Health Bethesda, MD, Nucleic Acids Research, vol. 25, No. 17, 1997, pp. 3389-3402.
Baldrick, Paul, "Pharmaceutical Excipient Development: The Need for Preclinical Guidance," Covance Laboratories Ltd., Regulatory Toxicology and Pharmacology, vol. 32, 2000, pp. 210-218.
Charman, W.N., "Lipids, Lipophilic Drugs, and Oral Drug Delivery—Some Emerging Concepts," Department of Pharmaceutics, Victorian College of Pharmacy, Monash University (Parkville Campus), Journal of Pharmaceutical Sciences, vol. 89, No. 8, 2000, pp. 967-978.
Colello, Rocio et al., "First report of the distribution of Locus of Adhesion and Autoaggregation (LAA) pathogenicity sland in LEE-negative Shiga toxin-producing *Escherichia coli* isolates from Argentina," Microbial PathogenElesis, vol. 123, 2018, pp. 259-263.
Colello, Rocio et al., "Identification and detection of iha subtypes in LEE-negative Shigatoxin-producing *Escherichia coli* (STEC) strains isolated from humans, cattle and food," Heliyon, vol. 5, 2019, pp. 1-6.
Corpet, Florence, "Multiple sequence alignment with bierarcbical clustering," Laboratoire de Genetique Cellulaire, INRA Toulouse, Nucleic Acids Research, vol. 16, No. 22, 1988, pp. 10881-10890.
Dickinson, B.L. et al., "Dissociation of *Escherichia coli* Heat-Labile Enterotoxin Adjuvanticity from ADP Ribosyltransferase Activity," Department of Microbiology and Immunology, Tulane University Medical Center, Infection and Immunity, vol. 63, No. 5, 1995, pp. 1617-1623.
Henikoff, Steven et al., "Amino acid substitution matrices from protein blocks," Howard Hughes Medical Institute, Basic Sciences Division, Fred Hutchinson Cancer Research Center, Proc. Natl. Acad. Sc. USA, vol. 89, 1992, pp. 10915-10919.

(Continued)

*Primary Examiner* — Jennifer E Graser
(74) *Attorney, Agent, or Firm* — Procopio, Cory, Hargreaves & Savitch LLP (57) ABSTRACT

Disclosed is an immunogenic formulation that induces protection against Shiga Toxin-Producing *Escherichia coli* (STEC), the formulation comprising: one or more chimeric proteins derived wholly or in part from OmpT and Hes proteins of STEC; and at least one physiologically or pharmaceutically acceptable excipient, carrier and/or diluent.

9 Claims, 2 Drawing Sheets

Specification includes a Sequence Listing.

(56) References Cited

OTHER PUBLICATIONS

Higgins, D.G et al., "CLUSTAL: a package for performing multiple sequence alignment on a microcomputer," Department of Genetics, Trinity College, Gene, vol. 73,1988, pp. 237-244.

Higgins, D.G. et al., "Fast and sensitive multiple sequence alignments on a microcomputer," Department of Genetics, Trinity College, Cabios Communications, vol. 5, No. 2, 1989, pp. 151-153.

Huang, Xioqiu et al., "Parallelization of a local similarity algorithm," Department of Computer Science, Michigan Technological University, Houghton, CABIOS, vol. 8, No. 2, 1992, pp. 155-165.

Montero, David et al., "Immunoproteomic Analysis To Identify Shiga Toxin-Producing *Escherichia coli* Outer Membrane Proteins Expressed during Human Infection," Infection and Immunity, vol. 82, No. 11, 2014, pp. 4767-4777.

Monteo, David et al., "Locus of Adhesion and Autoaggregation (LAA), a pathogenicity island present in emerging Shiga Toxin-producing *Escherichia coli* strains," Scientific Reports, 2017; 7: 7011, 13 pp. DOI:10.1038/s41598-017-06999-y.

Montero, David et al., Supplementary information—"Locus of Adhesion and Autoaggregation (LAA), a pathogenicity sland present in emerging Shiga Toxin-producing *Escherictlia coli* strains," Scientific Reports, 2017; 7: 7011, 12 pp. DOI:10. i 038is41598-017-06999-y.

Montero, David et al., "Cumulative acquisition of pathogenicity islands has shaped virulence potential and contributed to the emergence of LEE-negative Shiga toxin-producing *Escherichia coli* strains," Emerging Microbes & Infections, 2019, https://doi.org/10.1080/22221751.2019.1595985, pp. 485-502.

Montero, David et al., "Immunization of mice with chimeric antigens displaying selected epitopes confers protection against intestinal colonization and renal damage caused by Shiga toxin-producing *Escherichia coli*," Nature Partner Journals, vol. 20, 2020, pp. 1-13.

Needleman, S.B., "A General Method Applicable to the Search for Similarities in the Amino Acid Sequence of Two Proteins," Department of Biochemistry, Northwestern University, and Nuclear Medicine Service, V.A. Research Hospital, J. Mol. Biol, vol. 48, 1970, pp. 443-453.

Pearson, William, "Using the FASTA Program to Search Protein and DNA Sequence Databases," Methods in Molecular Biology, vol. 24, 1994, pp. 307-331.

Pearson, William et al., "Improved tools for biological sequence comparison," Department of Biochemistry, University of Virginia, Charlottesville, Proc. Natl. Acad. Sci., USA, vol. 85, 1988, pp. 2444-2448.

Rojas-Lopez, Maricarmen et al., "Intestinal Pathogenic *Escherichia coli*: Insights for Vaccine Development," Frontiers In Microbiology, vol. 9, Article 440, 2018, pp. 1-17.

Skeiky, Y.A., et al., "A Recombinant Leishmania Antigen that Stimulates Human Peripheral Blood Mononuclear Cells to Express a Th1-Type Cytokine Profile and to Produce Interleukin 12," Infectious Disease Research Institute, J. Exp. Med., vol. 181, 1995, pp. 1527-1537.

Smith, T.F. et al., "Comparison of Biosequences," Northern Michigan University, Los Alamos Scientific Laboratory, Advances in Applied Mathematics, vol. 2, 1981, pp. 482-489.

Torres, A.N. et al., "Deciphering Additional Roles for the EF-Tu, L-Asparaginase II and OmpT Proteins of Shiga Toxin-Producing *Eschericha coli*," Microorganisms, vol. 8, No. 1184, pp. 1-16.

Velez, M.V. et al., "Distribution of Locus of Adhesion and Autoaggregation and hes Gene in STEC Strains from Countries of Latin America," Current Microbiology, vol. 77, 2020, pp. 2111-2117.

Wang, Wei, "Lyophilization and development of solid protein pharmaceuticals," International Journal of Pharmaceutics, vol. 203, 2000, pp. 1-60.

International Search Report for related PCT/IB2019/054554, mailed Sep. 4, 2019.

Written Opinion for related PCT/IB2019/054554, mailed Sep. 4, 2019.

\* cited by examiner

SEQUENCE LISTING

<160> NUMBER OF SEQ ID NOS: 2

<210> SEQ ID NO 1
<211> LENGTH: 262
<212> TYPE: PRT
<213> ORGANISM: Artificial Sequence
<220> FEATURE:
<223> OTHER INFORMATION: Chimeric protein

<400> SEQUENCE: 1

```
Ala Leu Asp Leu Ser Tyr Arg Tyr Leu Asp Ala Gly Asp Ala Ser Val
1               5                   10                  15

Ser Tyr Lys Asp Glu Trp Gly Asp Lys Tyr Lys Ser Lys Val Ser Gln
            20                  25                  30

Leu Asp Trp Lys Phe Asn Asn Ala Ala Ile Ile Lys Gly Ala Ile Asn
        35                  40                  45

Trp Asp Leu Met Pro Gln Ile Ser Ile Gly Ala Ala Gly Trp Thr Thr
    50                  55                  60

Leu Gly Ser Arg Gly Gly Asn Met Val Asp Gln Asp Trp Met Asp Ser
65                  70                  75                  80

Ser Asn Pro Gly Thr Trp Thr Asp Glu Ser Arg His Pro Asp Thr Gln
                85                  90                  95

Leu Asn Tyr Ala Asn Glu Phe Asp Leu Asn Ile Lys Gly Trp Leu Leu
```

```
            100                 105                 110
Asn Glu Pro Asn Tyr Arg Leu Gly Leu Met Ala Gly Tyr Gln Glu Ser
        115                 120                 125

Arg Tyr Ser Phe Thr Ala Arg Gly Gly Ser Tyr Ile Tyr Ser Ser Glu
        130                 135                 140

Glu Gly Phe Arg Asp Asp Ile Gly Ser Phe Pro Asn Gly Glu Arg Ala
145                 150                 155                 160

Ile Gly Tyr Thr Ser Val Leu Ser Leu Ser Asn Gln Arg Leu Ile Asp
                165                 170                 175

Gly Glu Gly Glu Trp Ala Asp Lys Tyr Lys Gly Gly Asp Asp His Asp
            180                 185                 190

Thr Val Phe Ser Gly Gly Ile Ala Ala Gly Tyr Asp Phe Tyr Pro Gln
        195                 200                 205

Phe Ser Ile Pro Val Arg Thr Glu Leu Glu Phe Tyr Ala Arg Gly Lys
        210                 215                 220

Ala Asp Ser Lys Tyr Asn Val Asp Lys Asp Ser Trp Ser Gly Gly Tyr
225                 230                 235                 240

Trp Arg Asp Asp Leu Lys Asn Glu Val Ser Val Asn Thr Leu Met Leu
                245                 250                 255

Asn Thr Tyr Tyr Asp Phe
            260

<210> SEQ ID NO 2
<211> LENGTH: 559
<212> TYPE: PRT
<213> ORGANISM: Escherichia coli

<400> SEQUENCE: 2

Ala Asp Lys Val Val Gln Ala Gly Ile Ile Asn Arg Asp Gly Tyr Gln
1               5                   10                  15

Ser Val Lys Ser Gly Gly Leu Ala Thr Gly Thr Ile Ile Glu Thr Val
            20                  25                  30

Asn Asp Gly Thr Leu Thr Asn Arg Thr Gln Leu Ser Lys Gly Ala Ser
        35                  40                  45

Met Val Leu Asn Gly Asp Val His Asp Asn Gln Ile Val Phe Gly
    50                  55                  60

Thr Ala Asn Gly Met Thr Ile Ser Thr Gly Leu Glu Leu Gly Pro Asp
65                  70                  75                  80

Ser Glu Glu Asn Thr Gly Gly Gln Trp Ile Gln Asn Gly Gly Ile Ala
                85                  90                  95

Gly Asn Thr Thr Val Thr Thr Asn Gly Arg Gln Val Val Leu Glu Gly
            100                 105                 110

Gly Thr Ala Ser Asp Thr Val Ile Arg Asp Gly Gly Gln Ser Leu
        115                 120                 125

Asn Gly Leu Ala Val Asn Thr Thr Leu Asn Asn Arg Gly Glu Gln Trp
        130                 135                 140

Val His Glu Gly Gly Val Ala Thr Gly Thr Ile Ile Asn Arg Asp Gly
145                 150                 155                 160

Tyr Gln Ser Val Lys Ser Gly Gly Leu Ala Thr Gly Thr Ile Ile Asn
                165                 170                 175

Thr Gly Ala Glu Gly Gly Pro Asp Ser Asp Asn Ser Tyr Thr Gly Gln
            180                 185                 190

Lys Val Gln Gly Thr Ala Glu Ser Thr Thr Ile Asn Lys Asn Gly Arg
        195                 200                 205
```

```
Gln Ile Ile Leu Phe Ser Gly Leu Ala Arg Asp Thr Leu Ile Tyr Ala
    210                 215                 220

Gly Gly Asp Gln Ser Val His Gly Arg Ala Leu Asn Thr Thr Leu Asn
225                 230                 235                 240

Gly Gly Tyr Gln Tyr Val His Arg Asp Gly Leu Ala Leu Asn Thr Val
                245                 250                 255

Ile Asn Glu Gly Gly Trp Gln Val Val Lys Ala Gly Ala Ala Gly
                260                 265                 270

Asn Thr Thr Ile Asn Gln Asn Gly Glu Leu Arg Val His Ala Gly Gly
            275                 280                 285

Glu Ala Thr Ala Val Thr Gln Asn Thr Gly Gly Ala Leu Val Thr Ser
    290                 295                 300

Thr Ala Ala Thr Val Ile Gly Thr Asn Arg Leu Gly Asn Phe Thr Val
305                 310                 315                 320

Glu Asn Gly Lys Ala Asp Gly Val Val Leu Glu Ser Gly Gly Arg Leu
                325                 330                 335

Asp Val Leu Asp Asp His Asp Thr Val Phe Ser Gly Gly Ile Ala Ala
                340                 345                 350

Gly Tyr Asp Phe Tyr Glu Ser His Ser Ala Gln Asn Thr Leu Val Asp
            355                 360                 365

Asp Leu Ser Leu Ser Asn Gln Arg Leu Ile Asp Gly Glu Gly Glu Trp
    370                 375                 380

Ala Asp Lys Tyr Gly Gly Thr Leu Ala Val Ser Ala Gly Gly Lys Ala
385                 390                 395                 400

Thr Ser Val Thr Ile Thr Ser Gly Gly Ala Leu Ile Ala Asp Ser Gly
                405                 410                 415

Ala Thr Val Glu Gly Thr Asn Ala Ser Gly Lys Phe Ser Ile Asp Gly
                420                 425                 430

Thr Tyr Leu Asp Ala Gly Asp Ala Ser Val Ser Tyr Lys Asp Glu Trp
            435                 440                 445

Gly Asp Ser Gly Gln Ala Ser Gly Leu Leu Leu Glu Asn Thr Thr Leu
    450                 455                 460

Gly Ser Arg Gly Gly Asn Met Val Asp Gln Asp Trp Met Asp Ser Ser
465                 470                 475                 480

Asn Gly Gly Ser Phe Thr Val Asn Ala Gly Gly Gln Ala Gly Asn Thr
                485                 490                 495

Thr Val Gly His Arg Gly Thr Leu Thr Leu Ala Gly Asn Thr Ser Leu
            500                 505                 510

Tyr Asp His Asn Asp Asn Thr Ser Asp Tyr Ala Gly Gly Ser Leu Ser
            515                 520                 525

Gly Arg Thr Gln Leu Ser Lys Gly Ala Ser Met Val Leu Asn Gly Asp
    530                 535                 540

Val Val Ser Thr Gly Asp Ile Val Asn Ala Gly Glu Ile Arg Phe
545                 550                 555
```

IMMUNOGENIC FORMULATION THAT INDUCES PROTECTION AGAINST SHIGA TOXIN-PRODUCING *ESCHERICHIA COLI* (STEC)

CROSS-REFERENCE TO RELATED APPLICATIONS

This application is a US national stage application of International Application PCT/IB2019/054554, filed May 31, 2019, the contents of which are incorporated by reference.

FIELD OF THE INVENTION

The present invention is related to the field of immunology and provides an immunogenic formulation for preventing or treating infectious diseases. In particular, it provides a vaccine against shiga toxin-producing *Escherichia coli* to be used in animal reservoir and human risk populations.

BACKGROUND OF THE INVENTION

*Escherichia coli* (*E. coli*) is a member of the Enterobacteriaceae family found in the gastrointestinal microbiota of humans and other warm-blooded animals. Most of this family are considered harmless, but some are responsible of serious infectious diseases in humans. Particularly, shiga toxin-producing *Escherichia coli* (STEC) are etiological agents of acute diarrhea, dysentery and hemolytic uremic syndrome (HUS), a clinical syndrome characterized by progressive renal failure that can be lethal or that might lead to lifelong sequelae.

Although STEC serotype O157:H7 is the most prevalent cause of sporadic outbreaks and cases of severe disease, STEC serogroups such as O26, O103 and O113 have been associated with similar outbreaks.

Currently, the treatment of STEC HUS is fundamentally a supportive care and the use of antibiotics is contraindicated because such treatment might favor a release of shiga toxins (Stx1 and/or Stx2), increasing the risk of developing HUS. Alternative therapies based on compounds that bind and block the Stx have been proposed. However, the results of these therapies have been unsuccessful.

Many vaccines have been tested in animal models, such as: recombinant forms of Stx, intimin and SpA, chimeras of subunits A and B of Stx1 and Stx2, and avirulent strains of O157:H7, but not very successfully. The only candidate tested in humans is one based on the fusion of the "O" polysaccharide of *E. coli* O157:H7 and the exotoxin A of *Pseudomonas aeruginosa* (O157-rEPA). However, these studies are exclusively directed to STEC O157:H7 and they have not included other serogroups/serotypes (non-O157).

For this reason, there is a need for a broad-spectrum vaccine which confers protection against a wider range of STEC serotypes than just O157.

Currently, vaccine candidates have been unsuccessful because the characterization of antigens has mainly focused on strains O157:H7 as possible targets of STEC vaccines, including Stx, determinants of serological classifications (O antigen and flagellum) and proteins encoded in the locus of enterocyte effacement (LEE). For example, the US 2010/0166788 of Novartis Vaccines & Diagnostic discloses several polypeptides that can be included in immunogenic compositions specific for pathogenic *E. coli* strains. The polypeptides have cellular locations which render them accessible to the immune system. The genes encoding the polypeptides were initially identified as being present in uropathogenic strain 536 but absent from non-pathogenic strains. This document describes isolated polypeptides but not an immunogenic formulation of chimeric proteins.

CN 101062410 of Army Medical University (former Third Military Medical University, PLA.) discloses a "poly valency fuse type enterorrhagia property *Escherichia coli* O157:H7 gene engineering vaccine, which comprises the following steps: adopting enterorrhagia property *E. coli* O157:H7 Vi antigen Shiga's toxin II; combining subunit, compact sticking element and III type secretory protein A; constructing fuse engineering bacteria through gene retooling method; proceeding high density ferment; proceeding a series of purity course; getting fuse protein molecule vaccine with high purity".

For these reasons, the main objective of this invention is to provide an immunogenic formulation that will substantially prevent or minimize infection caused by several STEC serogroups, where the most frequent serogroups associated with severe clinical symptoms of hemorrhagic diarrhea and HUS are O157, O26, O45, O91, O103, O104, O113, O111, O121, O145 and O174.

BRIEF DESCRIPTION OF THE INVENTION

The present invention comprises an immunogenic formulation that induces protection from or immunity against shiga toxin-producing *Escherichia coli* (STEC). In particular, the immunogenic formulation comprises one or more chimeric proteins derived from OmpT and Hes proteins of STEC. The immunogenic formulation of the present invention may also be used to prepare vaccines.

BRIEF DESCRIPTION OF THE DRAWINGS

In FIG. 1A and FIG. 1D, SDS-PAGE 12% polyacrylamide with Coomassie Blue stain, 2 μg of bovine serum albumin (BSA), chimeric protein Q1 and Q2 respectively and molecular weight marker (M) were loaded. In FIG. 1B and FIG. 1E a Western Blot Analysis with and anti-His mouse mAB IgG are shown. M. Molecular weight marker. FIG. 1C and FIG. 1F show hypothetical structures of each three-dimensional chimeric protein.

FIG. 2. Illustrates the reactivity of chimeric proteins against IgG and IgA present in HUS patients sera (n=20) determined by ELISA. The concentration of IgG (FIG. 2A) and IgA (FIG. 2B) antibodies specific for each protein is shown. Each point represents the average of two independent experiments performed in duplicate. The lines indicate the value of the median. Statistical significance was determined by Kruskal-Wallis test followed by Dunn's multiple comparison test. * $P<0.05$ and ** $P<0.005$.

DETAILED DESCRIPTION OF THE INVENTION

The present invention provides an immunogenic formulation that induces protection or immunity against shiga toxin-producing *Escherichia coli* (STEC). In particular, the present invention resides in an immunogenic formulation comprising: one or more chimeric proteins derived wholly or in part from OmpT and Hes proteins of STEC; and at least one physiologically or pharmaceutically acceptable excipient, carrier, diluent and/or adjuvant.

OmpT is an aspartyl protease found on the outer membrane of *E. coli* and is a housekeeping protease that degrades foreign peptide material that the bacteria encounters in its surrounding environment. The Hes protein is a new allelic variant that has been denominated as hemagglutinin from *E. coli* STEC (Hes). The hes gene is present in STEC LEE-negative strains associated with severe disease and not detected in commensal *E. coli* strains.

An immunogenic formulation is a composition that induces a cellular and/or humoral immune response. An immune response is a response of a cell of the immune system, such as a B cell, T cell, or monocyte, to a stimulus. In the present invention, the immune response is specific for an antigen that comprises at least one chimeric protein derived from OmpT and Hes proteins of STEC (an "antigen-specific response"). An immune response may be a T cell response, such as a CD4+ response or a CD8+ response, or a B cell response, and results in the production of specific antibodies.

Expressed in another way, the one or more chimeric proteins of the present invention are immunogenic proteins. An immunogenic protein or polypeptide comprises an allele-specific motif, an epitope, or other sequence such that the protein/polypeptide will bind a MHC molecule and induce an immune response.

In one embodiment, the chimeric protein may further comprise a sequence derived wholly or in part from α-Cah protein of STEC. Cah is a calcium-binding autotransporter protein involved in autoaggregation and biofilm formation.

In one example, the chimeric protein may have at least a 90% identity with the amino acid sequence of SEQ ID No. 1. Alternatively, the chimeric protein may have at least a 90% identity with the amino acid sequence of SEQ ID No. 2.

In one embodiment, the formulation may comprise more than one or a second chimeric protein, wherein one chimeric protein has an amino acid sequence having at least 90% identity with SEQ ID NO. 1, and another or a second chimeric protein has an amino acid sequence having at least 90% identity to SEQ ID No. 2. It will be appreciated that sequence identity may be about 90%, 91%, 92%, 93%, 94%, 95%, 96%, 97%, 98%, 99% or higher.

In such an embodiment, both or the two chimeric proteins may be present in a ratio of between 1:2 to 2:1 in the immunogenic formulation. For example, both or the two chimeric proteins may be present in a ratio of 1:1.

The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs, orthologs, or variants of a polypeptide will possess a relatively high degree of sequence identity when aligned using standard methods. The percentage sequence identity may be determined over the full length of the relevant sequence (e.g., over the full length of SEQ ID NO:1 or SEQ ID NO:2) or over a fragment thereof, e.g., at least 50, 100, 200, 300, 400 or 500 amino acid residues of SEQ ID NO:1 or SEQ ID NO:2.

Methods of alignment of sequences for comparison are well known in the art. Various programs and alignment algorithms are described in: Smith & Waterman, Adv. Appl. Math. 2:482, 1981; Needleman & Wunsch, Mol. Biol. 48:443, 1970; Pearson & Lipman, Proc. Natl. Acad. Sci. USA 85:2444, 1988; Higgins & Sharp, Gene, 73:237-44, 1988; Higgins & Sharp, CABIOS 5: 151-3, 1989; Corpet et al., Nuc. Acids Res. 16: 10881-90, 1988; Huang et al., Computer Appls. in the Biosciences 8, 155-65, 1992; and Pearson et al., Meth. Mol. Bio. 24:307-31, 1994. Altschul et al., J. Mol. Biol. 215:403-10, 1990, presents a detailed consideration of sequence alignment methods and homology calculations.

The NCBI Basic Local Alignment Search Tool (BLAST) (Altschul et al., Mol. Biol. 215:403, 1990) is available from several sources, including the National Center for Biotechnology Information (NCBI, Bethesda, MD) and on the internet, for use in connection with the sequence analysis programs BLASTP, BLASTN, BLASTX, TBLASTN and TBLASTX. A description of how to determine sequence identity using this program is available on the NCBI website on the internet. The BLAST and the BLAST 2.0 algorithm are also described in Altschul et al., Nucleic Acids Res. 25:3389-3402, 1997. Software for performing BLAST analyses is publicly available through the National Center for Biotechnology Information (ncbi.nlm.nih.gov). The BLASTP program (for amino acid sequences) uses as defaults a word length (W) of 3, and expectation (E) of 10, and the BLOSUM62 scoring matrix (see Henikoff & Henikoff, Proc. Natd. Acad. Sci. USA 89: 10915, 1992).

The formulation of the present invention includes at least one physiologically or pharmaceutically acceptable excipient, carrier, diluent and/or adjuvant. Such carriers, excipients, and other agents that are incorporated into formulations provide improved transfer, delivery, tolerance, and the like. A multitude of appropriate formulations may be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTINT™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al "Compendium of excipients for parenteral formulations" PDA (1998) J Pharm Sci Technol 52:238-311.

By "adjuvant" is meant any substance that is used specifically or non-specifically to potentiate an antigen-specific immune response, perhaps through activation of antigen presenting cells. Examples of adjuvants include an oil emulsion (e.g., complete or incomplete Freund's adjuvant), Montanide incomplete Seppic adjuvant such as ISA, oil in water emulsion adjuvants such as the Ribi adjuvant system, syntax adjuvant formulation containing muramyl dipeptide, aluminum salt adjuvant (ALUM), polycationic polymer, especially polycationic peptide, especially polyarginine or a peptide containing at least two LysLeuLys motifs, especially KLKLLLLLKLK, immunostimulatory oligodeoxynucleotide (ODN) containing non-methylated cytosine-guanine dinucleotides (CpG) in a defined base context (e.g., as described in WO 96/02555) or ODNs based on inosine and cytidine (e.g., as described in WO 01/93903), or deoxynucleic acid containing deoxy-inosine and/or deoxyuridine residues (as described in WO 01/93905 and WO 02/095027), especially Oligo(dIdC)13 (as described in WO 01/93903 and WO 01/93905), neuroactive compound, especially human growth hormone (described in WO 01/24822), or combinations thereof, a chemokine (e.g., defensins 1 or 2, RANTES, MIP1-α, MIP-2, interleukin-8, or a cytokine (e.g., interleukin-1β, -2, -6, -10 or -12; interferon-γ; tumor necrosis factor-α; or granulocyte-monocyte-colony stimulating factor), a muramyl dipeptide variant (e.g., murabutide, threonyl-MDP or muramyl tripeptide), synthetic variants of MDP, a heat shock protein or a variant, a variant of *Leishmania major* LeIF (Skeiky et al., 1995, J. Exp. Med. 181: 1527-1537), non-toxic variants of bacterial ADP-ribosylating exotoxins (bAREs) including variants at the trypsin cleavage site (Dickenson and Clements, (1995) Infection and Immunity 63 (5): 1617-1623) and/or affecting ADP-ribosylation or chemically detoxified bAREs (toxoids), QS21, Quill A, N-acetylmuramyl-L-alanyl-D-isoglutamyl-L-alanine-2-[1,2-dipalmitoyl-s-glycero-3-(hydroxyphosphoryloxy)]ethylamide (MTP-PE) and compositions containing a metabolizable oil and an emulsifying agent. An adjuvant may be administered with an antigen or may be administered by itself, either by the same route as that of the antigen or by a different route than that of the antigen. A single adjuvant molecule may have both adjuvant and antigen properties.

The formulation may comprise one or more chimeric proteins as described herein above in combination with medical injection buffer and/or with adjuvant. Alternatively, or in addition, the formulation may comprise the one or more chimeric proteins in an aqueous buffered solution at a pH of between 6 and 8, e.g., 6.0 to 6.6, 6.4 to 7.1, 6.9 to 7.6 or 7.4 to 8.0.

An immunogenic formulation of the invention will be formulated to be compatible with its intended route of administration. Methods to accomplish the administration are known to those of ordinary skill in the art. It may also be possible to create compositions which may be topically or orally administered, or which may be capable of transmission across mucous membranes. For example, the administration may be intravenous, intraperitoneal, intramuscular, intracavity, subcutaneous, or transdermal.

Solutions or suspensions used for intradermal or subcutaneous application typically include at least one of the following components: a sterile diluent such as water, saline solution, fixed oils, polyethylene glycol, glycerine, propylene glycol, or other synthetic solvent; antibacterial agents such as benzyl alcohol or methyl parabens; antioxidants such as ascorbic acid or sodium bisulfite; chelating agents such as ethylenediaminetetraacetic acid (EDTA); buffers such as acetate, citrate, or phosphate; and tonicity agents such as sodium chloride or dextrose. The pH can be adjusted with acids or bases. Such preparations may be enclosed in ampoules, disposable syringes, or multiple dose vials.

Solutions or suspensions used for intravenous administration include a carrier such as physiological saline, bacteriostatic water, Cremophor EL™ (BASF, Parsippany, N.J.), ethanol, or polyol. In all cases, the formulation must be sterile and fluid for easy syringability. Proper fluidity can often be obtained using lecithin or surfactants. Such a formulation must also be stable under the conditions of manufacture and storage. Prevention of microorganisms may be achieved with antibacterial and antifungal agents, e.g., parabens, chlorobutanol, phenol, ascorbic acid, thimerosal, etc. In many cases, isotonic agents (sugar), polyalcohols (mannitol and sorbitol), or sodium chloride may be included in the formulation. Prolonged absorption of the formulation may be accomplished by adding an agent which delays absorption, e.g., aluminum monostearate and gelatin.

Formulations for oral delivery include an inert diluent or edible carrier. The formulation may be enclosed in gelatin or compressed into tablets. For the purpose of oral administration, the immunogenic protein(s) may be incorporated with excipients and placed in tablets, troches, or capsules. Pharmaceutically compatible binding agents or adjuvant materials can be included in the formulation. The tablets, troches, and capsules may contain (1) a binder such as microcrystalline cellulose, gum tragacanth or gelatin; (2) an excipient such as starch or lactose, (3) a disintegrating agent such as alginic acid, Primogel, or corn starch; (4) a lubricant such as magnesium stearate; (5) a glidant such as colloidal silicon dioxide; or (6) a sweetening agent or a flavoring agent.

Formulations may also be administered by a transmucosal or transdermal route. For example, some proteins may be capable of crossing mucous membranes in the intestine, mouth, or lungs. Transmucosal administration may be accomplished through the use of lozenges, nasal sprays, inhalers, or suppositories. Transdermal administration may also be accomplished through the use of formulations including ointments, salves, gels, or creams known in the art. For transmucosal or transdermal administration, penetrants appropriate to the barrier to be permeated are used. For administration by inhalation, formulations may be delivered in an aerosol spray from a pressured container or dispenser, which contains a propellant (e.g., liquid or gas) or a nebulizer.

The formulation may also contain other active compounds providing supplemental, additional, or enhanced therapeutic functions, such as one or more antibiotic or antibacterial agents, particularly those selective for Gram negative bacterial and/or *E. coli*.

The formulation may be included in a container, pack, or dispenser and/or in kits, together with instructions for administration.

It will be appreciated that the immunogenic formulation of the present invention may be used in the treatment or prophylactic treatment of STEC infection, or for use in the manufacture of a medicament for the treatment or prophylactic treatment of STEC infection. The invention also relates to the immunogenic formulation as described herein for use (in the manufacture of a medicament) for inducing an immune response in a patient.

Expressed in another way, the invention encompasses a method of treating or preventing an STEC infection, or inducing an immune response, the method comprising administering to a subject in need thereof a therapeutically effective amount of the immunogenic formulation described herein. Alternatively, the invention also reside in a method of treating or preventing infection by STEC or a disorder associated with STEC infection, in a subject, comprising, administering to the subject an immunogenic formulation as described herein, in an amount sufficient to inhibit or reduce STEC infection in the subject, thereby treating or preventing the infection or related disorder.

The term "treatment" refers to a therapeutic or preventative (prophylactic) measure, or passive immunization. The treatment may be administered to a subject who is already infected, or who ultimately may acquire or be at risk of acquiring such an infection, in order to prevent, cure, delay, reduce the severity of, or ameliorate one or more symptoms of the infection or a disorder or recurring disorder associated with the infection, or to prolong the survival of a subject beyond that expected in the absence of such treatment.

A "therapeutically effective amount" is the amount of agent, such as the immunogenic formulation disclosed herein that is sufficient to prevent, treat (including prophylaxis), reduce and/or ameliorate the symptoms and/or underlying causes of a disorder or disease, for example to prevent, inhibit, and/or treat an infection. In some embodiments, a therapeutically effective amount is sufficient to reduce or eliminate a symptom of a disease, such as an infection. For instance, this can be the amount necessary to inhibit or prevent bacterial replication or to alter measurably outward symptoms of the bacterial infection. In general, this amount will be sufficient to inhibit measurably bacterial replication or infectivity.

It is understood that to obtain a protective immune response against a pathogen may require multiple administrations of the immunogenic formulation. Thus, a therapeutically effective amount encompasses a fractional dose that contributes in combination with previous or subsequent administrations to attaining a protective immune response. For example, a therapeutically effective amount of an agent may be administered in a single dose, or in several doses, for example daily, during a course of treatment (such as a prime-boost vaccination treatment). However, the therapeutically effective amount may depend on the subject being treated, the severity and type of the condition being treated, and the manner of administration. A unit dosage form of the agent may be packaged in a therapeutic amount, or in multiples of the therapeutic amount, for example, in a vial (e.g., with a pierceable lid) or syringe having sterile components.

Formulations of the invention may be administered in therapeutically effective amounts as described. Therapeutically effective amounts may vary with the subject's age, condition, sex, and severity of medical condition. Appropriate dosage may be determined by a physician based on clinical indications. The formulations may be given as a bolus dose to maximize the circulating levels of immunogen for the greatest length of time. Continuous infusion may also be used after the bolus dose.

As used herein, the term "subject" is intended to include human and non-human animals. Subjects may include a human patient having a disorder characterized by STEC infection. The term "non-human animals" of the invention includes all vertebrates, such as non-human rodents, camelids, primates, sheep, dogs, cows, chickens, amphibians, reptiles, etc.

Examples of dosage ranges that may be administered to a subject may be chosen from: 1 μg/kg to 20 mg/kg, 1 μg/kg to 10 mg/kg, 1 μg/kg to 1 mg/kg, 10 μg/kg to 1 mg/kg, 10 μg/kg to 100 μg/kg, 100 μg to 1 mg/kg, 500 μg/kg to 1 mg/kg.

It may be advantageous to formulate compositions in dosage unit form for ease of administration and uniformity of dosage. Dosage unit form as used herein refers to physically discrete units suited for the patient or subject. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, the aforesaid antibody may be contained in about 5 to about 100 mg and in about 10 to about 250 mg for the other dosage forms. Thus, each dosage unit contains a predetermined quantity of immunogenic agent calculated to produce a therapeutic effect in association with the carrier. The dosage unit depends on the characteristics of the immunogenic agent and the particular therapeutic effect to be achieved.

Toxicity and therapeutic efficacy of the formulation may be determined by standard pharmaceutical procedures in cell cultures or experimental animals, e.g., determining the $LD_{50}$ (the dose lethal to 50% of the population) and the $ED_{50}$ (the dose therapeutically effective in 50% of the population).

Various delivery systems are known and may be used to administer the formulation of the invention. Methods of introduction include, but are not limited to, intradermal, intramuscular, intraperitoneal, intravenous, subcutaneous, intranasal, epidural, and oral routes. The formulation may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration may be systemic or local.

The formulation of the present invention may be administered with one or more additional active agents. Such additional agents may be administered together, separately or sequentially with the immunogenic formulation of the present invention. Separate administration refers to two compositions or active ingredients being administered at different times, e.g., at least 10, 20, 30, or 10-60 minutes apart, or 1, 2, 3, 4, 5, 6, 7, 8, 9, 10, 12 hours apart. One may also administer active ingredients at 24 hours apart, or even longer apart. Alternatively, two or more active ingredients may be administered simultaneously, e.g., less than 10 or less than 5 minutes apart. Compositions administered simultaneously may, in some aspects, be administered as a mixture, with or without similar or different time release mechanism for each of the components.

In methods of treatment described herein, one or more doses may be administered. In some cases, a single dose may be effective to achieve a long-term benefit. Thus, the method may comprise administering a single dose of the formulation. Alternatively, multiple doses may be administered, usually sequentially and separated by a period of days, weeks or months.

In another embodiment, the immunogenic formulation of the present invention may also be used to generate antibodies. Thus, the present invention relates to a method for inducing immunity in an animal, such as a mammal, against shiga toxin-producing *E. coli* (STEC) or pathology caused by STEC comprising administering the immunogenic formulation as described herein to the animal. Expressed in another way, there is provided the immunogenic formulation as described herein for use in inducing immunity against shiga toxin-producing *E. coli* (STEC) or pathology caused by STEC in an animal.

Encompassed within this is also a method for protecting an animal, such as a mammal, against infection of shiga toxin-producing *E. coli* (STEC) or pathology caused by STEC comprising administering an immunogenic formulation to the animal. Alternatively, there is provided the immunogenic formulation as described herein for use in protecting an animal, such as a mammal, against shiga toxin-producing *E. coli* (STEC) or pathology caused by STEC in the animal.

In this embodiment, the animal is one suitable for the production and harvesting of suitable antibodies generated by the animal in response to the immunogenic protein. Suitable animals include rodent, camelids and some sharks. It will be appreciated that the immune response of the animal may "primed" by way of pre-treatment with an adjuvant to increase the desired immune response to a later administered immunogenic agent. Alternatively or in addition, immune response of the animal may be "enhanced" through co-administration of an adjuvant and an immunogenic agent, wherein the adjuvant increases the desired immune response to the immunogenic agent compared to administration of the immunogenic agent to the subject in the absence of the adjuvant. Methods of generating antibodies in animals is well known in the art.

In a yet further embodiment, there is provided a chimeric protein derived from OmpT and Hes proteins of STEC comprising immunogenic epitopes, the chimeric protein having an amino acid sequence as set out in SEQ ID No. 1.

In another embodiment, the chimeric protein further comprises a sequence derived wholly or in part from α-Cah protein of STEC and having the amino acid sequence as set out in SEQ ID No. 2.

The invention will now be illustrated by the following non-limiting examples which are not restrictive of the invention as claimed. The accompanying figures constitute a part of this specification and, together with the description, serve only to illustrate embodiments and not limit the invention.

EXAMPLES

Example 1. To Determine if the Chimeric Proteins Q1 and Q2 Will be Recognized by Specific IgG and IgA Class Antibodies Present in HIS Sera The immunogenic formulation of the present invention comprises one or more chimeric proteins that includes at least one epitope of OmpT, α-Cah and Hes. Chimeric protein Q1 comprises a fusion of OmpT and Hes proteins, while the Q2 chimeric protein comprises carrier protein α-Cah which has been modified and includes in its structure epitopes of OmpT and Hes.

Twenty sera from convalescent pediatric patients who presented a prodrome of diarrhea within 20 days prior to the diagnosis of HUS were used; and two sera from patients without a clinical history of HUS were used as control sera.

The chimeric proteins Q1 and Q2 were prepared with a ?85% of purity percentage. Then, the genes coding for these proteins were optimized for their expression in $E.\ coli$ and cloned in the plasmid pET30a, allowing the addition of a Tag of 6 histidine residues at the N-terminal end of the protein a Tag of 6 histidine and a processing site for TEV protease. The strain $E.\ coli$ BL21 (DE3) strain was transformed with the resulting plasmids and recombinant colonies were selected in agar LB containing kanamycin.

The induction of protein synthesis was carried out by growing the recombinant bacteria in TB medium (Terrific Broth) containing kanamycin at 37° C. and, when the culture reached an $OD_{600}$ of 1.2, the culture was complemented with isopropyl β-D-1-thiogalactopyranoside (IPTG) for 4 hours. Bacteria were collected by centrifugation and resuspended in lysis buffer followed by sonication. After centrifugation, the sediment was dissolved using urea and was centrifugated again. The supernatant was used for purification of the protein. The denatured proteins were purified by Immobilized Metal Chelate Affinity Chromatography (IMAC-Ni affinity columns). The white proteins were renatured, sterilized in 0.22 μm filters and stored in aliquots. The protein concentration obtained was determined by Bradford assay using bovine serum albumin (BSA) as standard. The purity of the proteins was analyzed by densitometry on SDS-PAGE (FIGS. 1A and 1D). Additionally, it was confirmed that the purified proteins had the expected molecular weight by Western Blot using a developed anti-His monoclonal antibody.

ELISA microplates (96-well) (Nunc Immobilizer Amino Plates, ThermoFisher) were incubated with 1.2 μg of each protein diluted in 100 μl of phosphate buffered saline solution (PBS, pH 7.2) overnight at 4° C. Then, to make the standard curve, purified human IgG (Cat. 02-7102, Invitrogen) or IgA (Cat. 3860-1AD-6, Mabtech) was diluted in PBS from 5 μg/ml to 0.0048 μg/ml or from 0.1 μg/ml to 0.00019 μg/ml, respectively, overnight at 4° C. The plates were washed 3 times with PBS (400 μl/well) containing 0.05% Tween 20 (T-PBS). They were then incubated with 300 μl/well of blocking solution (T-PBS+0.5% bovine serum albumin) for 15 min at room temperature. Patient sera were diluted 1:1000 or 1:500 in blocking solution (100 μl/well) and incubated for 60 min at 37° C. After 5 washes with T-PBS (400 μl/well), Human Anti-IgG (H+L) (conjugated with peroxidase, developed in goat) (Cat. 04-10-06, KPL Inc) or iHuman Anti-IgA alpha chain (conjugated with alkaline phosphatase, developed in goat) (Cat. Ab97212, Abeam), diluted 1:1000 in blocking solution (100 μl/well) were incubated for 60 min at 37° C. After 5 washes with Tris saline solution (TBS) (400 μl/well, pH 7.5) containing 0.05% Tween 20, plates were incubated with the substrate 2,2'-azino-di (3-ethylbenzthiazoline-6-sulfonate) (100 μl/well; ABTS Peroxidase Substrate, Cat. 50-66-18, KPL Inc) or p-nitrophenyl phosphate (100 μl/well, pNPP Substrate, Cat. N2600-10, USBiological) for 10 or 20 min at room temperature, respectively. The reaction was stopped with 5% sodium dodecyl sulfate or 3M sodium hydroxide dissolved in distilled water (100 μl/well). The absorbance of the solution in each well was determined at 405 nm using a Synergy HT microplate reader (Biotek Instruments, USA). Each sample was determined in duplicate and with at least two independent experiments. The relationship between the absorbance values and the IgG or IgA concentration of each sample and control was calculated from each corresponding standard curve using a 4-parameter logistic regression equation determined in the GraphPad Prism 7 software.

Figure 1:
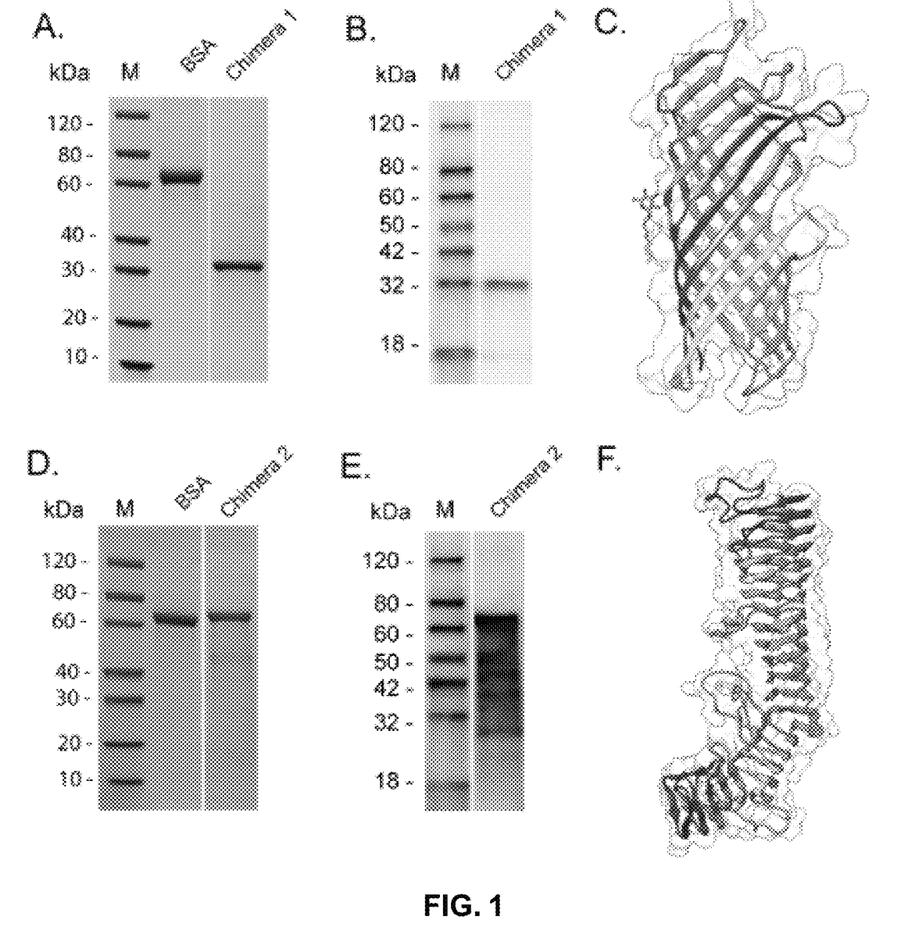
FIG. 1. Illustrates the densitometries of the Chimeric Proteins Q1 and Q2.

Results:

The reactivity of the two chimeric proteins, hereinafter referred to as chimeric protein 1 (Q1) and chimeric protein 2 (Q2), was determined against IgG and IgA present in 20 HUS sera and 2 control sera by ELISA (FIG. 1). Additionally, a peptide of 6 histidines (His-Tag) was included as a negative control.

As seen in FIG. 1, all the chimeras, Q1 and Q2 were sero-reactive to HUS sera but not to control sera.

Figure 2:
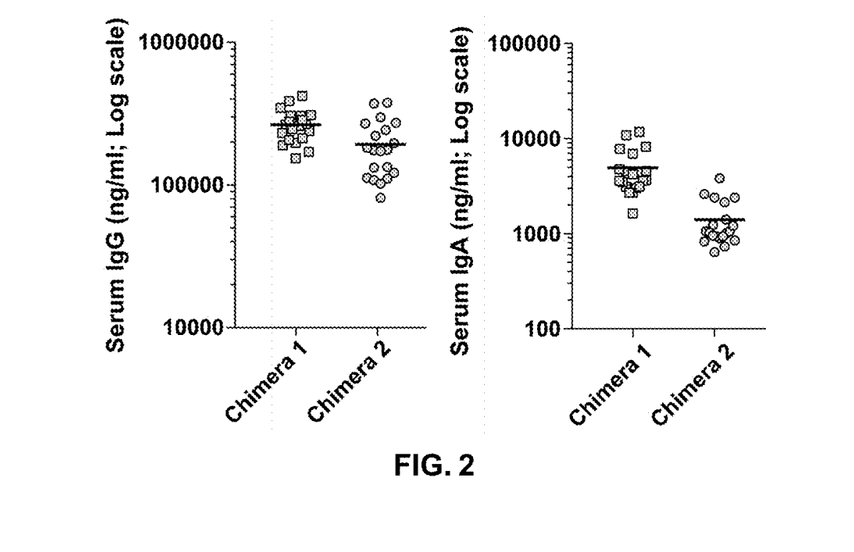

Particularly, in the case of IgG, Q1 was more sero-reactive (average=253 μg/ml, p<0.005) compared to Q2 (average=174 μg/ml). Similarly, in the case of IgA again Q1 had a higher level of sero-reactivity (average=4.871 ng/ml, p<0.005) compared to Q2 (average=1.390 ng/ml), see FIG. 2.

These results indicate that Q1 and Q2 chimeras were recognized specifically by antibodies class IgG and IgA present in HUS sera, with Q1 being the one with the highest sero-reactivity chimeric protein.

Example 2. Infection Tests in Mouse Model with STEC Strains

BALB/c females whose age ranged between 5-6 weeks were randomly distributed in 7 experimental groups with food and water ad libitum.

Of the 7 groups, 6 were immunized with 20 μg of each vaccinal antigen (Q1, Q2 and an equimolar mixture of both chimeras—hereafter named Q3), using as adjuvants Inject Alum (IA, Thermo Fisher Scientific) for intramuscular immunizations (IM) (50 μl) and Sigma Adjuvant System® oil (Sigma-Aldrich, SA) for intranasal immunizations (IN) (20 μl). The remaining group was immunized only with PBS, negative control. All experimental groups were immunized 3 times with 15-day intervals as shown in the following table:

TABLE 1

Summary of the three immunizations routes and the adjuvants used.

| Group | 1° | 2° | 3° |
|---|---|---|---|
| Group 1 | 20 µg Q1 + I.A (I.M) | 20 µg Q1 + I.A (I.M) | 20 µg Q1 (I.M) |
| Group 2 | 20 µg Q1 + S.A (I.M) | 20 µg Q1 + S.A (I.M) | 20 µg Q1 (I.M) |
| Group 3 | 20 µg Q2 + I.A (I.M) | 20 µg Q2 + I.A (I.M) | 20 µg Q2 (I.M) |
| Group 4 | 20 µg Q2 + S.A (I.M) | 20 µg Q2 + S.A (I.M) | 20 µg Q2 (I.M) |
| Group 5 | 20 µg Q3 + S.A (I.M) | 20 µg Q3 + I.A (I.M) | 20 µg Q3 (I.M) |
| Group 6 | 20 µg Q3 + S.A (I.M) | 20 µg Q3 + S.A (I.M) | 20 µg Q3 (I.M) |
| Group 7 | PBS + I.A (I.N) + S.A (I.M) | PBS + I.A (I.M) + S.A (I.N) | PBS (I.M) + PBS (I.N) |

Figure 3:
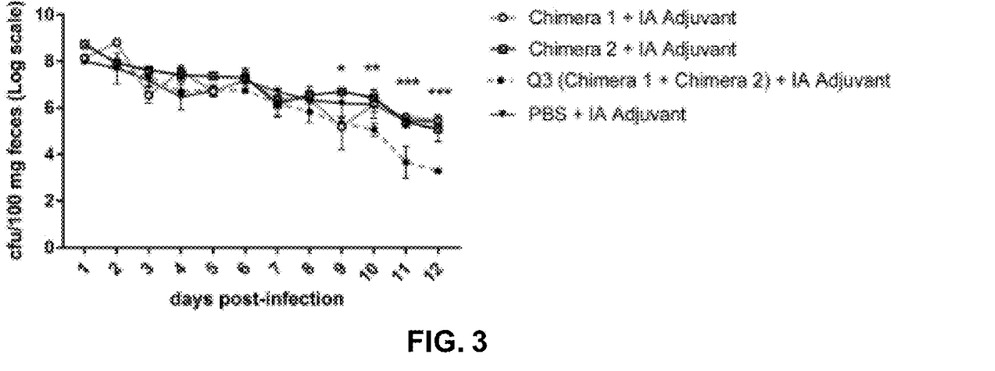
FIG. 3. Illustrates a summary of the colony forming units (CFU) count of *E. coli* O157:H7 in feces of mice that were immunized intramuscularly with the different proteins plus Imject™ Alum Adjuvant, subsequently the mice were infected orally. Each point shows the mean±SD of 4 mice. IA: Inject Alum Adjuvant. Statistical significance is represented by * ($P<0.05$).

Results:

CFU count in mice immunized with Imject Alum Adjuvant challenged with *E. coli* O157:H7: To determine the effectiveness of the different vaccine antigens; mice were infected with 109 CFU/ml of *E. coli* O157:H7 and feces were collected daily for 12 days. FIG. 3 shows the results obtained from the different vaccine antigens administered intramuscularly mixed with Imject Alum Adjuvant. FIG. 3 shows a progressive decrease in the bacterial load in the feces, establishing a significant difference from day 8 between the group immunized with Q3 versus the control and the other groups.

Figure 4:
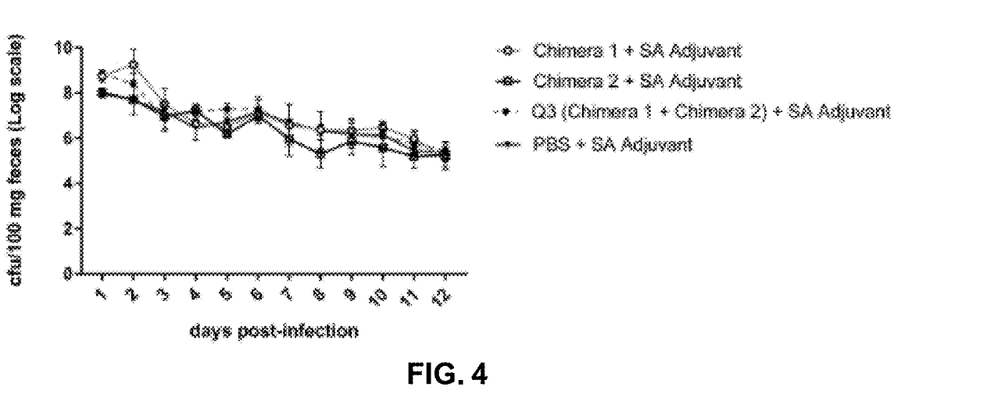
FIG. 4. Illustrates a summary of the CFU count of *E. coli* O157:117 in feces of mice that were immunized intranasally with the different proteins plus Sigma Adjuvant System, subsequently the mice were infected orally. Each point shows the mean±SD of 4 mice. SA: Sigma Adjuvant. Statistical significance is represented by * ($P<0.05$).

CFU count in mice immunized with an adjuvant (Sigma Adjuvant System) challenged with *E. coli* O157:H7: To determine the effectiveness of the different vaccine antigens, fresh feces were collected from the challenged mice for 12 days on a daily basis. FIG. 4 shows the results obtained from the different vaccine antigens administered intranasally mixed with Sigma Adjuvant System.

In FIG. 4 shows that on day 2 post challenge, the feces of the mice immunized with Q1 contained a significantly higher amount of CFU of *E. coli* O157:H7 (9.2 log CFU/100 mg), compared with the control group (7.6 log UFC/100 mg). After that, the CFU decreased without presenting significant differences compared to the control.

In summary, seven immunogenic proteins present in STEC strains of different serogroups and/or serotypes were identified in O26:H11, O103, O113: H21 and O157:H7. Notably, these proteins are absent in the commensal *E. coli* HS strain and are reactive to sera from patients who developed HUS (HUS sera). The antigens OmpT and α-Cah proteins showed seroreactivity to immunoglobulins IgG and IgA class in HUS sera, but not in control sera, obtained from patients not infected with STEC. In addition, the prevalence of genes encoding these two proteins is statistically higher in STEC strains associated with severe disease than in commensal *E. coli* strains. Additionally, the protein initially identified as Hek, later characterized as a new allele of the family of heat-resistant agglutinin proteins (Hra) and shows reactivity against IgG and IgA in HUS sera (unpublished results). This new allelic variant was denominated as hemagglutinin from *E. coli* STEC (Hes). The hes gene is present in STEC LEE-negative strains associated with severe disease. Conversely, in commensal *E. coli* strains the gene was not detected. Consequently, considering the seroreactivity and distribution of the coding genes in a variety of STEC serotypes associated with severe disease, the OmpT, α-Cah and Hes antigens may form the basis for an immunogenic formulation developed as a vaccine against this pathotype.

The invention claimed is:

1. An immunogenic formulation that induces protection against shiga Toxin-Producing *Escherichia coli* (STEC), the formulation comprising:
   (i) a chimeric protein derived from OmpT and Hes proteins of STEC, having the amino acid sequence as set forth in SEQ ID NO: 1;
   (ii) a second chimeric protein derived from α-Cah protein of STEC, having the amino acid sequence as set forth in SEQ ID NO: 2; and
   (iii) at least one physiologically or pharmaceutically acceptable excipient, carrier and/or diluent.

2. The immunogenic formulation according to claim 1, wherein both chimeric proteins are present in the formulation at a ratio of between 1:2 to 2:1.

3. The immunogenic formulation according to claim 2, wherein both chimeric proteins are present in the formulation at a ratio of 1:1.

4. The immunogenic formulation according to claim 1 for use in treatment or prophylactic treatment of STEC infection or a disorder associated with STEC infection, or inducing an immune response to STEC.

5. A method of treatment or prophylactic treatment of STEC infection or a disorder associated with STEC infection, the method comprising administering to a subject a therapeutically effective amount of an immunogenic formulation as claimed in claim 1.

6. A method for inducing immunity in an animal, such as a mammal, against shiga toxin-producing *E. coli* (STEC) or pathology caused by STEC comprising administering an immunogenic formulation as claimed in claim 1 to the animal.

7. A method for protecting an animal, such as a mammal against infection with Shiga toxin-producing *E. coli* (STEC) or pathology caused by STEC comprising administration of an immunogenic composition as in claim 1 to the animal.

8. A chimeric protein derived from OmpT and Hes proteins of shiga toxin-producing *E. coli* (STEC) comprising immunogenic epitopes having the amino acid sequence as set forth in SEQ ID NO: 1.

9. A chimeric protein derived from α-Cah protein of shiga toxin-producing *E. coli* (STEC) comprising the amino acid sequence as set forth in SEQ ID NO: 2.

* * * * *